United States Patent [19]

Nicklasson

[11] Patent Number: 5,431,922
[45] Date of Patent: Jul. 11, 1995

[54] METHOD FOR ADMINISTRATION OF BUSPIRONE

[75] Inventor: Alf G. M. Nicklasson, Södertälje, Sweden

[73] Assignee: Bristol-Myers Squibb Company, New York, N.Y.

[21] Appl. No.: 145,723

[22] Filed: Oct. 28, 1993

Related U.S. Application Data

[63] Continuation of Ser. No. 803,300, Dec. 4, 1991, abandoned, which is a continuation-in-part of Ser. No. 665,924, Mar. 5, 1991, abandoned.

[51] Int. Cl.⁶ .......................... A61K 9/28; A61K 9/26
[52] U.S. Cl. .................................. 424/490; 424/484; 424/486; 424/487; 424/489
[58] Field of Search ............... 424/484, 486, 487, 489, 424/490

[56] References Cited

U.S. PATENT DOCUMENTS

| | | | |
|---|---|---|---|
| 3,717,634 | 2/1973 | Wu et al. | 514/252 |
| 4,182,763 | 1/1990 | Casten et al. | 424/251 |
| 4,634,703 | 1/1987 | Kurtz et al. | 514/252 |
| 4,640,921 | 2/1987 | Othmer et al. | 514/252 |
| 4,663,150 | 5/1987 | Pandz | 424/497 X |
| 4,704,284 | 11/1987 | Beatty | 424/469 |
| 4,764,380 | 8/1988 | Urguhart | 424/465 |

FOREIGN PATENT DOCUMENTS 1350255 4/1974 Sweden.

OTHER PUBLICATIONS

Krowczynski, *Extended Release Dosage Forms*, CRC–Press, Inc. 1987 (3/3; 3/15), 1–7, 10–17 and 97–100.
Mayol, et al., *Clin Pharmacol. Ther.*, 37, 210, 1985 (4/18; 4/34).
Gammans, et al., *American J. Med.*, 80, Suppl. 3B, 41, 1986 (4/22).
Robinson, et al., *Controlled Drug Delivery: Fundamentals and Applications*, Marcel Dekker Inc., 1987 (6/16, 6/26), pp. 23–26.
Johansson, et al., *Acta Pharm. Suec.*, 8, 59, 1971 (6/23).
Martin, *Psychopharmacology* (1991) 104: 275–278.

*Primary Examiner*—Thurman K. Page
*Assistant Examiner*—Raj Bawa
*Attorney, Agent, or Firm*—Richard P. Ryan

[57] ABSTRACT

An improved method for administering buspirone comprises oral administration of controlled/extended release formulations of buspirone and salts thereof which require from about 6 to 24 hours for in vitro dissolution of at least 80% of the buspirone content. Administration of these formulations increases buspirone bioavailability in relation to its major metabolite. Improved efficacy, drug tolerability and patient convenience result from this improved method of administration.

12 Claims, No Drawings

METHOD FOR ADMINISTRATION OF BUSPIRONE

CROSS REFERENCE

This is a continuation of application Ser. No. 07/803,300 filed on Dec. 4, 1991 now abandoned, which is a continuation-in-part of application U.S. Ser. No. 07/665,924 filed Mar. 5, 1991 now abandoned.

FIELD OF THE INVENTION

The present invention relates to a method of administering oral controlled/extended release dosage forms of buspirone and its salts in order to obtain a drug delivery system of buspirone which will provide a less frequent dosing during the day, e.g. a once daily dosing with a minimum of undesired side-effects. These formulations also deliver a higher ratio of buspirone, compared with its metabolite, into the general circulation. This produces a beneficial pharmaceutical effect compared to administration of conventional immediate release oral formulations.

BACKGROUND OF THE INVENTION

The physicochemical, pharmacokinetic and pharmacological properties of drugs and their products will often dictate how they should be used in a therapeutic situation. A drug characterized by a short biological half-life should be administered in short dosing intervals to maintain the plasma concentration levels that provide the pharmacologic action. This often reduces patient compliance and as a result leads to underdosing between the dosage intervals. An ideal oral dosage form would be a once-daily formulation able to maintain the therapeutic drug levels in the body for 24 hours, yet without the risk of any adverse reactions. The use of controlled/extending release dosage forms in drug therapy has been increasing in recent years with a concomitant tendency toward once-a-day dosing formulations. Listings of controlled/extended release products and their design can be rather extensive (L. Krowczynski, *Extended Release Dosage Forms*, CRC-Press Inc., USA, 1987, ISBN 0-8493-4307-0).

Among formulations devised to avoid limitations due to a short biological half-life (rapid metabolism/elimination) have been technically developed dosage forms which provide release of the desired drug over an extended period of time, thereby slowing the drug's absorption. Over the past two decades considerable progress has been made in developing controlled/extended release technologies for drug compounds. The design of various controlled/extended release formulations and their technologies are known in the art (L. Krowczynski, *Extended Release Dosage Forms*, CRC-Press Inc., USA, 1987, ISBN 0-8493-4307-0).

Some important advantages of such delivery systems are:
- reduction of the frequency of dosing (with a concomitant increase in patient compliance);
- maintenance of therapeutic plasma drug levels for a longer period of time than would be indicated by the drug's biological half-life;
- reduction of undesired adverse reactions/toxicity (by suppresion of the initial high plasma concentration peak);
- reduction of the amount of drug required for treatment (also provided by reducing the very high initial plasma concentrations).

Buspirone, an azaspirondecanedione, with the structural formula

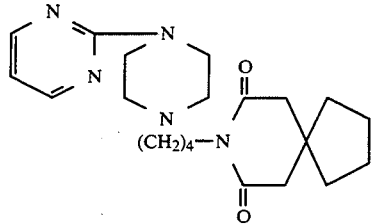

Buspirone, chemically: 8-[4-[4-(2-pyrimidinyl)1-piperazinyl]butyl]-8-azaspiro(4,5)-decane-7,9-dione (disclosed in U.S. Pat. No. 3,717,634) is a pharmaceutically active compound which has been found to be effective for the treatment of anxiety disorders and depression. However, buspirone shows a very high first pass metabolism and only about 4% of a therapeutic dose will reach the systemic circulation unchanged after oral administration (Mayol et al., Clin Pharmacol. Ther., 37, 210, 1985). Great interindividual variations in buspirone absorption have also been observed as demonstrated by variations of the maximum plasma concentration of drug by up to 10-fold (Gammans et al., American J. Med., 80, Suppl. 3B, 41–51, 1986). Metabolites have been identified, including several hydroxylated derivatives of buspirone that show little pharmacological activity and the major metabolite; 1-(2-pyrimidinyl)-piperazine, (1-PP), which has been found in its own right to be about 20–25% as potent an anxiolytic agent as buspirone in pharmacologic testing.

The biological half-life of buspirone is very short and variable in man, on an order of 2–11 hours, whereas the much less active metabolite, 1-PP, has much slower elimination (Mayol et al., Clin Pharmacol. Ther., 37, 210, 1985). These pharmacokinetic properties necessitate a rather frequent daily dosing regimen which would be expected to have a negative effect on patient compliance. Since buspirone is rapidly absorbed after an oral dose, high peak plasma values occur shortly after drug administration and these are associated with the occurrence of undesired or adverse events observed during the first days of treatment. These adverse effects can also seriously impact patient compliance due to resultant deliberate disruption of the drug therapy. Since its clinical introduction, buspirone has suffered from a perceived lack of immediate effect and much of this may be attributable to patient compliance. Patient monitoring evidences inappropriate dosing—either using buspirone as a night-time dose or taking it prn.

An initial object of this invention was to provide for administration oral controlled/extended release dosage forms of buspirone wherein desirable pharmacologic blood levels, i.e. not too high or too low, of the pharmacologically active component (unmetabolized buspirone) were maintained in the patient's systemic circulation. Such a pharmacokinetic profile contrasts with that following administration of conventional immediate release tablets where initial high peak plasma concentrations of buspirone (with adverse effects) and rapid elimination were experienced. The object then was to be able to increase the time intervals between drug dosing while retaining effectiveness and yet improve drug tolerability at the same time.

Because buspirone has complicated pharmacokinetics with extensive first pass metabolism, attempts to modify buspirone oral absorption, e.g. to simplify the daily dosing without the risk of underdosing between each time of administration, by means of an extended release delivery system which would minimize undesired side effects; had never been undertaken.

It is well known to one skilled in the art that extensive or complex metabolism of a drug makes the design of an oral controlled/extended release product very difficult. It has been shown in the literature that reductions in systemic availability due to metabolism during the absorptive process can be greater for controlled/extended release drug dosage forms than for immediate release drug products. Hence, it has been claimed that drugs which undergo extensive first pass clearance are unsuitable for oral controlled/extended release dosing (J. R. Robinson and V. H. L. Lee, *Controlled Drug Delivery: Fundamentals and Applications*, Marcel Dekker Inc., USA, 1987, ISBN 0-8247-7588-0). It has also been shown in the literature that metabolism of a drug, e.g. alprenolol, was more complete when it was administered in a controlled/extended release form than in conventional tablets (R. Johansson, C. G. Regårdh and J. Sjögren, *Acta Pharm, Suec.*, 8, 59 (1971)). Many other similar examples have been reviewed in the literature (J. R. Robinson and V. H. L. Lee, *Controlled Drug Delivery: Fundamentals and Applications*, Marcel Dekker Inc., USA, 1987, ISBN 0-8247-7588-0).

With these pharmacokinetic disclosures and the variable extensive oral metabolism of buspirone, it was not apparent that a desirable pharmacokinetic profile could be obtained by development of oral extended-release formulations of buspirone. It was completely unexpected that not only was the bioavailability of buspirone increased but, in addition, the ratio of buspirone to 1-PP plasma levels would be significantly increased due to lower plasma levels of 1-PP that result following administration of controlled/extended release oral formulations of buspirone.

SUMMARY OF THE INVENTION

The invention concerns an improved method for administration of the useful drug buspirone. The method comprises oral administration of buspirone via controlled/extended-release pharmaceutical formulations which show at least 80% drug dissolution between 6 and 24 hours. Administration of the formulations result in an increase in buspirone blood levels with a concomitant decrease in blood levels of its major metabolite 1-pyrimidin-2-ylpiperazine (1-PP). This unexpected increase in drug concentration ratio of unchanged buspirone to metabolite in systemic circulation is even more significant in light of studies which indicate that certain of buspirone's desirable pharmacologic actions can be antagonized by 1-PP. Additionally, the dosing interval is lengthened and drug tolerability is improved and these effects promote patient compliance.

DETAILED DESCRIPTION OF THE INVENTION

Buspirone shows an extensive first pass metabolism with a ten-fold variation between subjects. With this metabolic pattern in relation to the above-mentioned examples and general statements from the literature regarding suitability of such drugs for controlled/extended release dosage forms; it is understandable why no prior attempts to design an oral controlled/extended release product of buspirone have been reported.

As part of the present invention it has now been found possible to extend the oral absorption phase of buspirone while modulating initial high plasma peak values by administering buspirone in controlled/extended release formulations. The plasma concentrations of buspirone were found to be extended and constant for periods of at least 18 hours after a 30 mg single dose and, during a 24 hour test period in vivo, a very high tolerability was observed compared to the administration of conventional buspirone tablets (3×10 mg). Furthermore, the mean relative extent of buspirone bioavailability was found to be increased up to 5 to 6-fold compared to administration of conventional dosage forms of buspirone.

The present invention provides an improved method for oral delivery of buspirone compared to using conventional immediate release oral formulations. Different formulation technologies can be applied for controlling and extending the release of buspirone (and hence its absorption in vivo) such as, for example, matrix formulations and multicompartment formulations (capsules or tablets containing pellets or microcapsules). The invention relates to various in vitro release time courses within each type of formulation technology by employing various types and combinations of pharmaceutical excipients and polymers. The present invention comprises all oral controlled/extended release formulations of buspirone which are able to show a total in vitro dissolution time between 6 and 24 hours for at least 80 per cent of the drug content. The in vitro dissolution time is measured by means of the USP XXI paddle method at 50 or 100 rpm. This method gives results in accordance with the flow-through method using water at a flow rate of 16 ml/minute.

Another object of the invention which has been realized with the improved method of administration is a greater tolerability of buspirone. Extending the release of buspirone by employing oral controlled/extended release formulations that demonstrate on in vitro dissolution time of between 6 and 24 hours for at least 80 per cent of the drug, results in a marked decrease of unwanted side-effects in human subjects. Cross-over comparisons of buspirone administration in a clinical population given similar strength doses of buspirone via extended release and via conventional release formulations demonstrated clear superiority in tolerance for extended release formulations of buspirone. The dizziness and light-headed feelings most commonly reported following conventional buspirone administration were eliminated or suppressed in most subjects when given buspirone by the improved method of this invention.

The most unexpected aspect of the improved method of buspirone administration is the increase in plasma concentration of unchanged drug with a concomitant decrease in the major metabolite, 1-PP. This result is counter-intuitive to pharmacokinetic expectations, given buspirone's rapid extensive first-pass metabolism and clearance. This surprising effect is most clearly expressed by looking at the ratio of blood level concentrations of unchanged buspirone to 1-PP, the predominate species. Regardless of whether the clinical population was undergoing acute or chronic dosing, methods of administration extending the release of buspirone resulted in increasing this ratio several-fold.

An increase in the buspirone to 1-PP ratio appears to be desirable from a therapeutic viewpoint in addition to the objectives already given for the invention. More recent pharmacologic studies indicate that the metabolite, 1-PP, can antagonize beneficial effects of buspirone. Social interaction paradigms that measure levels of anxiety have shown that 1-PP has an anxiogenic effect when administered to diazepam-withdrawn animals. Previous studies had not shown any effect of 1-PP on social interaction in diazepam-naive subjects. Azapirone anxiolytics, such as buspirone, have failed to adequately treat patients undergoing diazepam-withdrawal, a common condition in populations of anxious patients. These experiments produce evidence that increased anxiogenesis and loss of efficacy in this specific patient population can be attributed to 1-PP. This is surprising in light of 1-PP's (weak) antianxiety activity observed in previous animal testing.

In studies of depression, buspirone was tested systemically and intracerebrally in a rat forced swim test which is a useful screening procedure for antidepressant agents. Buspirone was active when given intracerebrally, but inactive when given systemically. The activity of intracerebral buspirone could be blocked by systemic administration of 1-PP thereby demonstrating its antagonism of buspirone's antidepressant effect. On the basis of these and other studies, the improved method of buspirone administration which increases the ratio of unchanged buspirone to 1-PP would be expected to enhance the desired anxiolytic and antidepressant effects of buspirone. Thus the improved method of the instant invention produces a non-obvious therapeutic advantage over previous methods of orally administering conventional formulations of buspirone.

In regard to the controlled/extended release formulations of buspirone to be employed in the improved method, considerable variation in formulations and components may be practiced without departing from the instant invention. Buspirone or any salt form thereof can be used, for instance: acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, (embonate), pantothenate, phosphate/diphosphate, polygalacturonate, salicylate, stearate, subacetate, succinate, sulphate, tannate, tartrate, teoclate, triethiodide. Hydrates are also included. The hydrochloride salt of buspirone is preferred however.

Various controlled/extended release technologies may be employed without departing from the invention as long as the required in vitro release characteristics of 80% dissolution within 6 to 24 hours are met. Various matrix-based systems, overcoated micropellet systems, and osmotically controlled systems all provide a basis for embodiments of formulations for use in the improved method. For the improved method of administration, matrix formulations and overcoated micropellets are preferred release-extending embodiments with matrix formulations being most preferred.

By either embedding the buspirone compound into a matrix formulation or overcoating it into a microcapsule formulation, or both, in order to control or extend the release, the following advantages are obtained compared to when conventional immediate release tablets are administered:

a slower in vivo absorption of buspirone and hence lower plasma peak values which reduce the occurrence of undesired side effects;

prolonged and constant buspirone plasma concentrations over 24 hours which will avoid underdosing between dosage intervals;

a therapeutically useful increase in the plasma level ratio of unchanged buspirone relative to the metabolite 1-PP;

a significant increase of the relative extent of buspirone bioavailability (i.e. the therapeutically relevant component);

much higher tolerability of the drug, i.e. much less side effects;

a once daily dosing of buspirone which together with the higher tolerability will increase patient compliance.

As coating or matrix adjuvant any coating or matrix material can be used. The type of material will be chosen depending on the desired controlled release time-function i.e. whether it will be a dosage form having a 6, 12 or 24 hour release time in vitro. The choice of coating or matrix material will in either case be obvious to one skilled in the art.

Coating and matrix materials which may be used are, for instance,

Polymers: synthetic polymers of polyvinyl type, e.g. poly vinylchloride, polyvinylacetate and copolymers thereof, polyvinylalcohol, polyvinylpyrrolidone.

Polyethylene type, e.g. polyethylene, polystyrene.

Polymers of acrylic acid or acrylic acid ester type, e.g. methylmethacrylate or copolymers of acrylic monomers.

Biopolymers or modified biopolymers of cellulose, e.g. ethylcellulose, cellulose acetate phthalate, cellulose acetate, hydroxy propyl cellulose, hydroxypropylmethyl cellulose, hydroxypropyl cellulose, methylcellulose, microcrystalline cellulose, Na-carboxymethyl cellulose; sodium alginate; chitosan.

Shellac

Gelatin

Fats, oils, higher fatty acids and higher alcohols e.g. aluminum monostearate, cetylalcohol, hydrogenated beef tallow, hydrogenated vegetable oil, hydrogenated castor oil, 12-hydroxystaryl alcohol, glyceryl mono- or dipalmitate, glyceryl mono- di-, or tristearate, myristyl alcohol, stearic acid, stearyl alcohol.

Polyethyleneglycols

Waxes e.g. bees wax, carnauba wax, Japan wax, paraffin, spermaceti, synthetic wax.

Sugars and sugar alcohols e.g. mannitol, sorbitol, sucrose, xylitol, glucose, maltose.

The polymers mentioned above can be used, depending on the technique, when applied as coating agents, matrix adjuvants or pharmaceutical binders. Whether the polymer will be a matrix adjuvant or a pharmaceutical binder will be dependant on the amount of polymer in the formulation.

Any combinations of the above-mentioned polymers, fats and waxes can be used for encapsulation purposes as well as for matrix formation, viz. different polymers can be mixed, a polymer can be mixed with a fat or wax etc.

The encapsulation of the drug can be achieved in the form of microcapsules, but the encapsulation is not restricted to the micro size.

The multiparticulate dosage forms, i.e. microcapsules or coated pellets as well as the matrix tablets useful for the present invention can be prepared by any of several acknowledged production processes including conventional granulation and tabletting of matrix tablets, pan coating, prilling, extrusion and spheronization, fluid bed processes, spray drying, spray chilling, coacervation and other processes.

Microcapsules or coated pellets

Microcapsules or coated pellets are defined as a solid or liquid core enclosed in a coating. The coating may also be referred to as the wall or shell. Various types of microcapsule structures can be obtained depending on the manufacturing process e.g. mononuclear spherical, multinuclear spherical, multinuclear irregular, encapsulated mononuclear capsules, dual-walled microcapsules etc. Where no distinct coating and core region can be observed, the analogous terms are microparticles, microspheres, micromatrices, micro beads. The microcapsules or pellets usually have a particle size between 1 and 2000 microns.

The microcapsules or coated pellets of buspirone and its salts can be filled into empty hard gelatine capsules to an extent corresponding to the desired dose or they can be gently compressed into a tablet by using suitable tablet excipients.

Buspirone or a salt thereof could be mixed with a pharmaceutical binder to form micropellets which are then compressed into tablets.

The oral formulation of the invention could comprise micropellets which are then overcoated with a pharmaceutically acceptable coating adjuvant prior to being compressed into tablets.

The micropellets can also be filled into capsules.

The oral formulation of the invention could comprise microspheres which are then overcoated with a pharmaceutically acceptable coating adjuvant prior to being filled into capsules.

Matrix Formulations

Matrix formulations are defined as a drug embedded in insoluble excipients in order to achieve extended release by a continuous leaching of the drug from the inert matrix core. The release mechanism often follows the square root law of Higuchi ($\sqrt{t}$-law). This term also applies to a matrix built of hydrophilic substances which in contact with water form a gel of high viscosity.

Preferred embodiments

Certain improved methods of the present invention for the oral administration of buspirone are preferred. One preferred embodiment of the present invention comprises administration of the formulation obtained when buspirone hydrochloride is embedded in polyvinyl chloride and polyvinyl acetate and then compressed into a tablet formulation using magnesium stearate as lubricant (round tablet, 6–8 mm in diameter).

Other preferred embodiments employ pharmaceutical formulations obtained when buspirone hydrochloride is embedded in polyvinyl chloride and ethyl cellulose by the addition of hydroxypropyl methyl cellulose, sodium carboxymethyl cellulose or paraffin. The material is then compressed into tablets using magnesium stearate as lubricant.

Still other preferred embodiments result from using formulation wherein buspirone hydrochloride is mixed with a sugar derivative e.g. lactose and/or a cellulose derivative e.g. microcrystalline cellulose to obtain uncoated microspheres by means of extrusion and spheronization. The microspheres are then overcoated with e.g. ethyl cellulose using a suitable plasticizer e.g. triethyl citrate. The microcapsules can be filled into empty hard gelatine capsules.

Additional preferred embodiments involve administration of formulations in which buspirone is suspended in a wax melt, e.g. carnauba wax, bees wax etc. and then spray chilled into microspheres. The spherical particles can then be overcoated with a fat or fatty acid, polyethylene glycol or a low melting wax by suspending the microspheres in the low melting excipient and then once again spray chill the slurry into microcapsules.

The most preferred embodiment comprises oral administration of formulations of buspirone hydrochloride compounded with hydroxypropylmethylcellulose, povidone and stearic acid.

DESCRIPTION OF SPECIFIC EMBODIMENTS

The pharmaceutical compositions and formulations which make up the controlled/extended release dosage forms of buspirone adapted for use in the improved method of administration which constitutes this invention, will appear more fully from a consideration of the following examples which are given for the purpose of illustration only and are not to be construed as limiting the invention in sphere or scope.

EXAMPLE 1

Buspirone hydrochloride was dry mixed with polyvinyl chloride. The powder mixture was then granulated with a solution of polyvinyl acetate in ethanol. After drying and milling, the granulation was compressed into 7 mm round tablets.

The buspirone controlled release tablets consist of

|  | (mg/tablet). |
|---|---|
| Buspirone hydrochloride | 30 |
| Polyvinyl chloride | 120 |
| Polyvinyl acetate (C10-V7) | 11 |
| Magnesium stearate | 1.6. |

The in vitro dissolution was investigated in water by means of the USP XXI paddle method at different agitation conditions. The results are shown in Table 1.

TABLE 1

| | Range (% dissolved, n = 6) | |
|---|---|---|
| Time (hours) | 50 rpm | 100 rpm |
| 1 | 34–35 | 32–39 |
| 3 | 57–58 | 53–57 |
| 5 | 71–73 | 67–71 |
| 8 | 84–88 | 81–87 |
| 12 | 92–96 | 90–95 |

This particular controlled release formulation of buspirone shows a 12 hour release time profile. As can be seen, a very uniform in vitro dissolution behavior with a low interindividual variation between the six different tablet units are obtained. Hence, the design of the dosage form seems to be very robust in terms of in vitro dissolution characteristics.

The in vivo absorption and drug tolerability of this particular formulation of buspirone (B-E/R) were studied in six healthy subjects. As a reference, the same drug dose of conventional immediate release buspirone (B-I/R) tablets was used, e.g. 3×10 mg, BUSPAR ®, Bristol-Myers Squibb, USA.

Table 2 shows typical plasma concentration levels of buspirone versus time for the two products tested in two different subjects. As can be seen, significant different plasma profiles are obtained from administration of different buspirone dosage forms. Administration of the controlled/extended release dosage form of buspirone shows much lower plasma concentration peaks, a slower rate of absorption and much more extended plasma concentration versus time courses compared to administration of the conventional tablet formulation of buspirone. Buspirone can be detected in plasma 24 hours after administration of the controlled/extended release formulation whereas no detectable buspirone concentrations can be found 4 to 8 hours after administration of the conventional immediate release tablets.

TABLE 2

| Time (h) | Administration of B-E/R (ng/ml) | | Administration of B-I/R (ng/ml) | |
|---|---|---|---|---|
| | Subj. 1 | Subj. 4 | Subj 1 | Subj. 4 |
| 0.5 | 1.87 | 1.41 | 2.28 | 4.04 |
| 1 | 2.33 | 1.80 | 0.89 | 2.96 |
| 2 | 2.33 | 2.12 | 0.58 | 0.85 |
| 4 | 1.44 | 1.72 | 0.40* | ND |
| 6 | 2.20 | 2.02 | 0.08* | ND |
| 8 | 1.56 | 2.13 | 0.08* | ND |
| 12 | 1.66 | 1.92 | ND | ND |
| 18 | 0.75 | 0.26* | ND | ND |
| 24 | 0.75 | 0.24* | ND | ND |

ND = not detected
* = below the lowest standard calibrator used in the assay (0.5 ng/ml).

Table 3 shows the relative extent of buspirone bioavailability for administration of the B-E/R tablet compared to administration of B-I/R formulation. Dose=30 mg.

TABLE 3

| Subject No. | Rel. extent of buspirone bioavilability (B-E/R to B-I/R) |
|---|---|
| 1 | 16.8 |
| 2 | 11.9 |
| 3 | 1.2 |
| 4 | 4.7 |
| 5 | 1.4 |
| 6 | 0.4 |

As can be seen, in 5 out of 6 subjects, a significant increase in buspirone bioavailability is obtained when buspirone is administered orally using the B-E/R formulation. Hence, the buspirone has become superbioavailable when administered by means of the exemplified controlled/extended release dosage form. Even though significantly higher amounts of buspirone enter the general circulation during the 24 hour time period following administration of controlled/extended release formulations, improved drug tolerability is also obtained by administering buspirone in a controlled/extended release dosage form according to the present invention.

Table 4 shows a comparison of observed side effects by subject following administration of single doses of 30 mg of buspirone given both conventionally and in accordance with the improved method.

TABLE 4

| Subject No. | Adverse experiences (severity)* following administration of: | |
|---|---|---|
| | B-E/R (Example 1) | B-I/R |
| 1 | Frontal headache (2) | None |
| 2 | None | Dizziness & light-headed (2) |
| 3 | None | Dizziness & paraesthesia (1) |
| 4 | None | Dizziness (2) |
| 5 | None | Dizziness & paraesthesia in both hands, dizziness postural in nature. Nausea on sitting up (3) |
| 6 | None | None |

*(1) = mild
(2) = moderate
(3) = severe

It is evident that the instant method of buspirone administration results in an improvement in the therapeutic application of buspirone in terms of drug tolerability.

As demonstrated supra, buspirone bioavailability is significantly improved through the present invention. However, another positive effect resulting from the present invention is a decrease of the bioavailability of the major metabolite 1-PP. For administration of B-E/R, much lower plasma peak values of 1-PP and a slower rate of the increase of its plasma concentrations are seen. This effect may also be a contributing factor to the improved tolerability observed after administration of buspirone according to the present invention. Table 5 summarizes the relative extent of 1-PP bioavailability after administration of the buspirone controlled/extended release tablet according to Example 1, compared to administration of a conventional tablet formulation.

TABLE 5

| Subject No. | Rel. extent of 1-PP bioavilability following administration of B-E/R |
|---|---|
| 1 | 0.7 |
| 2 | 0.5 |
| 3 | 0.4 |
| 4 | 0.9 |
| 5 | 0.7 |
| 6 | 1.1 |

EXAMPLE 2

Buspirone hydrochloride was dry mixed with polyvinyl chloride. The powder mixture was then granulated with polyvinyl acetate dissolved in ethanol. After drying and milling, the granulation was compressed into round matrix tablets with a diameter of 8 mm.

The buspirone controlled release matrix tablets consist of:

| | (mg/tablet) |
|---|---|
| Buspirone hydrochloride | 30 |
| Polyvinyl chloride | 160 |
| Polyvinyl acetate | 20 |
| Magnesium stearate | 2.1 |

The in vitro dissolution was determined in water by means of the USP XXI Paddle method at various agitation conditions, see Table 6.

TABLE 6

| Time (hours) | Range (% dissolved, n = 6) | |
|---|---|---|
| | 50 rpm | 100 rpm |
| 1 | 19–20 | 22–23 |
| 3 | 35–36 | 36–39 |
| 5 | 44–46 | 48–50 |
| 8 | 56–58 | missing |
| 12 | 68–71 | 68–71 |
| 15 | 75–78 | 81–85 |
| 20 | 83–85 | 88–93 |
| 24 | >90 | >90 |

This particular controlled/extended release formulation of buspirone demonstrates a 24 hour release time course. As seen in Table 6, this formulation of buspirone shows a uniform in vitro dissolution behavior with a low interindividual variation between the six different tablet units which is in good agreement with the data shown in Example 1 for a 12 hours controlled release matrix tablet. Hence, as was mentioned before, the principle of embedding buspirone into a polyvinyl chloride/polyvinyl acetate matrix will produce a reliable controlled release drug delivery system which is unaffected by the hydrodynamic intensity.

The in vivo absorption and drug tolerability were also investigated for administration of this 24 hour time release formulation of buspirone. Six healthy subjects participated in the study using conventional immediate release tablets (3×10 mg), BUSPAR ®, Bristol-Myers Squibb, USA as reference.

Table 7 shows typical buspirone plasma concentration versus time data for two subjects following administration of the Example 2 controlled release formulation. As a reference, buspirone plasma concentration versus time data are also shown after administration of conventional buspirone tablets (BUSPAR ®, Bristol-Myers Squibb, USA) at a single dose of 30 mg.

TABLE 7

| | (ng/ml) B-E/R (Example 2) | | (ng/ml) B-I/R | |
|---|---|---|---|---|
| Time (h) | Subj. 4 | Subj. 5 | Subj 4 | Subj. 5 |
| 0.5 | 1.01 | 0.26* | 4.07 | 6.31 |
| 1 | 2.43 | 0.41* | 2.96 | 3.28 |
| 2 | 2.05 | 0.99 | 0.85 | 2.99 |
| 4 | 1.98 | 1.11 | ND | 1.49 |
| 6 | 2.31 | 0.97 | ND | 0.47* |
| 8 | 0.04* | 0.86 | ND | 0.22* |
| 12 | 0.87 | 1.03 | ND | 0.05* |
| 18 | 1.03 | 0.72 | ND | 0.09* |
| 24 | 1.80 | 0.74 | ND | 0.05* |

ND = not detected
* = below the lowest standard calibrator used in the assay (0.5 ng/ml).

As can be seen, much different plasma profiles were obtained. Again, administration of the controlled release formulation of buspirone shows much lower plasma concentration peaks, a slower rate of absorption and much more extended plasma concentration versus time courses of these parameters following administration of the conventional tablet formulation. Thus, even when the in vitro dissolution time is increased from 12 hours to 24 hours (cf. Example 1), a sufficient absorption of buspirone is achieved. After 24 hours, significant plasma concentration levels are found in the two subjects after administration of the Example 2 buspirone formulation, whereas no detectable concentrations or negligible levels were observed for the conventional dosage form from 4 to 8 hours after administration.

Table 8 shows the relative extent of buspirone bioavailability for the 24 hour release formulation of buspirone (Example 2) compared to the conventional tablet formulation (BUSPAR ®, 3×10 mg, Bristol-Myers Squibb, USA).

TABLE 8

| Subject No. | Rel. extent of buspirone bioavilability (B-E/R to B-I/R) |
|---|---|
| 1 | Missing data |
| 2 | 8.2 |
| 3 | 1.3 |
| 4 | 6.3 |
| 5 | 1.7 |
| 6 | 0.4 |

An increase of buspirone bioavailability can be seen following administration of the 24 hour controlled/extended release formulation which is in agreement with the absorption data found for the 12 hour release formulation in Example 1. The plasma concentrations in subject No. 1 were found to be detectable but below the lowest standard calibrator used in the assay, i.e. 0.5/ng/ml. This is the reason why the relative extent of buspirone bioavailability has not been given in Table 8. However, if the raw data are used in a calculation, a value of 2.8 is found for subject No. 1. It is only in subject No. 6 where a lower bioavailability can be seen which also is in agreement with the data shown in Example 1 (the same healthy subjects were used in both studies).

The adverse experiences observed following administration of the different buspirone formulations after a single dose of 30 mg are reported in Table 9.

TABLE 9

| | Adverse experiences (severity)* following administration of: | |
|---|---|---|
| Subject No. | B-E/R (Example 2) | B-I/R |
| 1 | None | None |
| 2 | None | Dizziness & light-headed (2) |
| 3 | None | Dizziness & paraesthesia (1) |
| 4 | None | Dizziness (2) |
| 5 | None | Dizziness & paraesthesia in both hands, dizziness postural in nature. Nausea on sitting up (3) |
| 6 | None | None |

*(1) = mild
(2) = moderate
(3) = severe

Once again, it is obvious that the present inventive method of administration of buspirone is a great improvement in the therapeutic application of buspirone in terms of drug tolerability.

Table 10 shows the corresponding bioavailability data for the 1-PP metabolite following administration of the B-E/R product of Example 2.

TABLE 10

| Subject No. | Rel. extent of 1-PP bioavilability following administration of B-E/R |
|---|---|
| 1 | 0.44 |
| 2 | 0.16 |

TABLE 10-continued

| Subject No. | Rel. extent of 1-PP bioavilability following administration of B-E/R |
|---|---|
| 3 | 0.16 |
| 4 | 0.70 |
| 5 | 0.78 |
| 6 | 1.02 |

The results displayed above in Examples 1 and 2 demonstrate the advantage of administering buspirone controlled/extended release formulations which provide either 12 hour or 24 hour drug release profiles. For both formulations, a significantly higher extention of buspirone bioavailabilities and a low frequence of side effects were obtained compared to a single dose administration of a conventional tablet formulation. Hence, the most optimum application of buspirone in a therapeutic situation would employ the improved method of administering a controlled/extended release product. Both 12 and 24 hour release formulations can be administered and result in extended plasma concentrations versus time course suitable for a once daily dosing regimen. The present invention will provide for a higher amount of the drug to enter the general circulation but with a much lower frequency of side effects. The invention will also protect against the underdosing that often occurs following administration of a conventional release formulation of buspirone. The once a day dosing regimen achieved by means of the present invention compared to the currently recommended three doses a day of the conventional market formulation (tablets) of buspirone will definitely make buspirone therapy more convenient for the patients and hence, an increase in patient compliance is to be expected.

EXAMPLE 3

Buspirone hydrochloride was dry-mixed with polyvinyl chloride. The powder mixture was granulated with a solution of polyvinyl acetate dissolved in ethanol. After drying and milling, the granulation was compressed into round matrix tablets with a diameter of 6 mm.

The buspirone controlled/extended release tablets consist of:

|  | (mg/tablet). |
|---|---|
| Buspirone hydrochloride | 15 |
| Polyvinyl chloride | 80 |
| Polyvinyl acetate | 7.3 |
| Magnesium stearate | 1.0. |

The in vitro dissolution data are presented in Table 11 using the USP XXI paddle method at 50 rpm (water).

TABLE 11

| Time (hours) | Range (% dissolved, n = 6) |
|---|---|
| 3 | 50-57 |
| 6 | 67-77 |
| 12 | 85-96 |

The present formulation relates to a 12 hour release product containing 15 mg buspirone hydrochloride per tablet.

EXAMPLE 4

Buspirone hydrochloride was dry-mixed with polyvinyl chloride and sodium carboxymethyl cellulose. The powder mixture was granulated with a solution of ethyl cellulose 10 cps dissolved in ethanol. After drying and milling, the granulation was compressed into tablets using magnesium stearate as lubricant (8 mm round tablets).

The buspirone controlled/extended release tablets consist of:

|  | (mg/tablet). |
|---|---|
| Buspirone hydrochloride | 30 |
| Polyvinyl chloride | 145 |
| Ethyl cellulose 10 cps | 10 |
| Sodium-carboxymethyl cellulose | 15 |
| Magnesium stearate | 1.95 |

Table 12 shows the in vitro dissolution characteristics for this particularly controlled release formulation of buspirone using the USP XXI paddle method at 50 rpm (water).

TABLE 12

| Time (hours) | Range (% dissolved, n = 3) |
|---|---|
| 1 | 26-32 |
| 2 | 47-52 |
| 6 | 85-94 |

As can be seen, the above formulation shows a 6 hour release time course of buspirone in vitro.

EXAMPLE 5

Buspirone hydrochloride was dry-mixed with lactose and microcrystalline cellulose. Water was added and the wet powder mass was extruded in a NICA-extruder using a 1 mm screen. The extrudates were spheronized on a marumerizer plate into microspheres to a size range of 0.8-1.4 mm. The wet microspheres were dried and then overcoated with ethyl cellulose 10 cps in a fluid bed apparatus. The ethyl cellulose was dissolved in a 6/4 mixture of methylene chloride and ethanol. Triethyl citrate was used as plasticizer in the polymer film.

The buspirone controlled/extended release microcapsules consist of the following. A 30 mg dosage strength (i.e. a hard gelatine capsule) is used in this particular Example. However, lower as well as higher dosage strengths can easily be obtained by decreasing or increasing the amount of microcapsules administered e.g. in a hard gelatine capsule.

|  | (mg/tablet). |
|---|---|
| Buspirone hydrochloride | 30 |
| Lactose | 180 |
| Microcrystalline cellulose | 120 |
| Ethyl cellulose 10 cps | 20 |
| Triethyl citrate | 2 |

Table 13 shows the in vitro dissolution results for the buspirone controlled/extended release microcapsules using the USP XXI paddle method at 50 rpm (water).

TABLE 13

| Time (hours) | Range (% dissolved, n = 3) |
|---|---|
| 1 | 20-22 |
| 3 | 51-53 |
| 6 | 72-74 |
| 12 | 88-90 |

As can be seen, buspirone can be formulated into a multiparticular controlled/extended release formulation showing, as in this Example, a 12 hour release time course in vitro.

EXAMPLE 6

Buspirone hydrochloride was compounded into differing strength tablets, according to Table 4, utilizing the standard procedures set forth supra.

TABLE 4

Composition of Sustained/Controlled Release Buspirone HCl Tablets of Varying Strength

| Component | 15 mg/tab | 20 mg/tab | 30 mg/tab |
|---|---|---|---|
| Buspirone HCl | 15.0 mg | 20.0 mg | 30.0 mg |
| Hydroxypropyl Methylcellulose, USP Type 2208, 100,000 cps | 201.0 mg | 201.0 mg | 201.0 mg |
| Providone | 6.7 mg | 6.7 mg | 6.7 mg |
| Colloidal Silicon Dioxide | 0.7 mg | 0.7 mg | 0.7 mg |
| Stearic Acid | 1.6 mg | 1.6 mg | 1.6 mg |
| Total Weight | 225.0 mg | 230.0 mg | 240.0 mg |

Steady state bioavailability of buspirone and 1-PP was compared in a 12 subject two-way crossover study. The subjects were administered either one 30 mg B-E/R tablet (Example 4) or 10 mg of conventional release buspirone formulation (BUSPAR®, Bristol-Myers Squibb Co.) three times per day for a 10-day period. Following a 7-day washout period the second 10-day treatment period utilized the alternate drug treatment (crossover). Blood samples for analysis were collected on day 10 of each treatment period. The attainment of steady state was verified by comparing the plasma concentrations of 1-PP prior to administration of the morning dose on study days 8, 9, and 10 of each treatment period. The mean buspirone CMAX peak was about 25% lower and the 1-PP CMAX peak about 18% lower with chronic administration of B-E/R compared to B-1/R. In addition the area under the curve from time 0 to 24 hour (AUC 0–24) was 18% higher for buspirone concentration and 30% lower for 1-PP concentration for the B-E/R compared to B-1/R administered chronically.

Adverse experiences were experienced following both B-E/R and B-1/R administration. There was a trend for fewer adverse events following administration of B-E/R.

In summary then, as demonstrated by pharmaceutical and clinical testing described in the above examples: oral administration of controlled/extended release buspirone pharmaceutical compositions with 80% drug dissolution occurring between 6 and 24 hours provide the following improvements and advantages in buspirone therapy:

a reduction in peak drug and metabolite plasma levels resulting in reduced side-effect potential;
  prolonged buspirone plasma concentrations that allow the convenience of once-a-day dosing but still maintain drug therapeutic effects;
  a significant increase in the ratio of buspirone to 1-PP concentrations that should provide an improvement in the desired therapeutic effects of buspirone.

I claim:

1. An improved method for administering buspirone comprising oral administration of buspirone, or a pharmaceutically acceptable salt thereof, in a controlled/extended release pharmaceutical formulation selected from the group of formulations consisting of buspirone or a salt thereof embedded in a matrix; buspirone or a salt thereof formed into micropellets; and buspirone or a salt thereof formed into coated micropellets; with the formulation requiring from about 6 to 24 hours for in vitro dissolution of at least 80% of the buspirone content.

2. An oral formulation for controlled/extended release of buspirone or a salt thereof wherein the formulation is selected from the group consisting of buspirone or a salt thereof embedded in a matrix; buspirone or a salt thereof formed into micropellets; and buspirone or a salt thereof formed into coated micropellets; with the formulation requiring from about 6 to 24 hours for in vitro dissolution of at least 80% of the buspirone content.

3. The improved method of claim 1 wherein the controlled/extended release formulation comprises buspirone or a salt thereof embedded in a pharmaceutically acceptable matrix adjuvant.

4. The improved method of claim 1 wherein the controlled/extended release formulation comprises buspirone or a salt thereof and a pharmaceutical binder formed into micropellets which are then tableted or filled into capsules.

5. The improved method of claim 4 wherein the micropellets are overcoated with a pharmaceutically acceptable coating adjuvant.

6. The improved method of claim 1 wherein the controlled/extended release formulation comprises buspirone hydrochloride.

7. The improved method of claim 3 wherein the matrix adjuvant is comprised of polymers selected from the group consisting of polyvinyl polymers, polyvinylpyrrolidone polymers, ethyl cellulose, sodium carboxymethylcellulose, hydroxypropylcellulose, and hydroxypropylmethylcellulose.

8. The improved method of claim 4 wherein the pharmaceutical binder is comprised of pharmaceutical binder materials selected from sugars, cellulose, cellulose ethers, hydroxypropylcellulose, and hydroxyproxylcellulose ethers.

9. The improved method of claim 7 wherein the matrix adjuvant is comprised of hydroxypropylmethylcellulose and polyvinylpyrrolidone.

10. The improved method of claim 1 wherein the controlled/extended release formulation is comprised, in parts by weight, of about 15 to 30 parts buspirone hydrochloride; about 200 parts hydroxypropylmethylcellulose; about 6 to 7 parts polyvinylpyrrolidone; about 1 part colloidal silicon dioxide; and about 1 to 2 part stearic acid.

11. The formulation of claim 2 comprising buspirone or a salt thereof embedded in a pharmaceutically acceptable matrix adjuvant.

12. The formulation of claim 2 comprising buspirone or a salt thereof and a pharmaceutical binder formed into micropellets which can be overcoated with a pharmaceutically acceptable coating adjuvant.

* * * * *